United States Patent [19]

Fäh

[11] 4,185,018
[45] Jan. 22, 1980

[54] PROCESS FOR PRODUCING BENZOFURAZAN-1-OXIDES

[75] Inventor: Hansjakob Fäh, Ettingen, Switzerland

[73] Assignee: Ciba-Geigy Corporation, Ardsley, N.Y.

[21] Appl. No.: 935,282

[22] Filed: Aug. 21, 1978

[51] Int. Cl.$^2$ .......................................... C07D 271/12
[52] U.S. Cl. .................................................... 548/126
[58] Field of Search ...................................... 260/307 D

[56] References Cited

U.S. PATENT DOCUMENTS

| | | | |
|---|---|---|---|
| 3,398,141 | 8/1968 | Haddadin et al. | 260/239.5 |
| 3,528,098 | 9/1970 | Shaw | 260/307 |
| 3,660,398 | 5/1972 | Ley et al. | 260/250 R |
| 3,900,473 | 8/1975 | Diel et al. | 260/250 Q |
| 3,996,259 | 12/1976 | Lee et al. | 260/465 B |

OTHER PUBLICATIONS

Lee et al., Tet. Letters (20), 1641–1644, 1976.
Mallory, Organic Syn IV, 74–78 (1963).
Krishnan et al., J. Amer. Chem. Soc., 99, 8121–8123 (1977).
Pehmlow Ang. Chem. Int. Ed. 13, 170–179 (1974).

Primary Examiner—Mark L. Berch
Attorney, Agent, or Firm—Karl F. Jorda; Harry Falber

[57] ABSTRACT

A process for the production of benzofurazan-1-oxides by reacting a 2-nitroaniline with alkali metal hypochlorite is disclosed which process comprises the performance of the reaction of the 2-nitroaniline with the alkalimetal hypochlorite in a two-phase reaction medium consisting of water and an organic solvent immiscible with water, in the presence of a phase-transfer catalyst.

11 Claims, No Drawings

PROCESS FOR PRODUCING BENZOFURAZAN-1-OXIDES

The present invention relates to a process for producing benzofurazan-1-oxides of the formula I

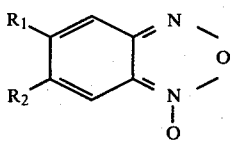

in which

R$_1$ and R$_2$ independently of one another each represents hydrogen, halogen, an alkyl group which has 1 to 4 carbon atoms and which can be substituted by halogen, hydroxyl, amino, alkylamino having 1 to 4 carbon atoms in the alkyl group and dialkylamino having 1 to 4 carbon atoms in each of the alkyl groups, or represents an alkoxy group having 1 to 4 carbon atoms, an alkylthio group having 1 to 4 carbon atoms, an alkoxycarbonyl group having 1 to 4 carbon atoms in the alkyl group, carbamoyl, N-alkylcarbamoyl having 1 to 4 carbon atoms in the alkyl group, N,N-dialkylcarbamoyl having 1 to 4 carbon atoms in each of the alkyl groups, sulfamoyl, N-alkylsulfamoyl having 1 to 4 carbon atoms in the alkyl group, N,N-dialkylsulfamoyl having 1 to 4 carbon atoms in each of the alkyl groups, a carboxyl group or a cyano group, and either the radical R$_1$ or the radical R$_2$ can additionally represent a group of the formula

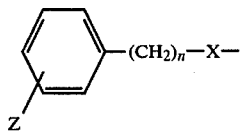

wherein Z represents hydrogen, halogen, an alkyl group having 1 to 4 carbon atoms, an alkoxy group having 1 to 4 carbon atoms, an alkylthio group having 1 to 4 carbon atoms or a trifluoromethyl group, n represents 0, 1 or 2, and X represents oxygen, sulfur, a sulfinyl group or a sulfonyl group, by reaction of 2-nitroanilines of the formula II

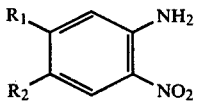

in which R$_1$ and R$_2$ have the meanings given under the formula I, with alkali metal hypochlorite.

The benzofurazan-1-oxides of the formula I are valuable intermediates for producing quinoxaline-1,4-dioxides having an antimicrobial action. The production of such quinoxaline-1,4-dioxides is described for example in the U.S. Pat. Nos. 3,398,141, 3,660,398 and 3,900,473.

The method of producing benzofurazan-1-oxides of the formula I by oxidation of 2-nitroanilines of the formula II with alkali metal hypochlorite is known (see Org. Synth., Vol. IV, page 74 ff, (1963)). This process comprises introducing an aqueous alkali metal hypochlorite solution into an alcoholic solution of 2-nitroaniline. Although the benzofurazan-1-oxides of the formula I are obtained by this process in good yields, the process does have a number of disadvantages which greatly reduce the feasibility of it being carried out on a commercial scale. Thus, for example, there are formed from the alcohol used as solvent and the alkali metal hypochlorite thermally unstable esters of hypochlorous acid, which can decompose in an explosive manner. Furthermore, the benzofurazan-1-oxides of the formula I which are produced by the aforementioned process have to be isolated from the reaction mixture and dried. This procedure is disadvantageous not only because it is complicated but also because it constitutes a considerable danger to safety on account of the thermal instability of the benzofurazan-1-oxides of the formula I. A further disadvantage is that the waste-water of the process contains a large amount of alcohol, and the necessary separation of this for ecological reasons is both involved and expensive.

The object of the present invention is therefore to provide a process for producing benzofurazan-1-oxides of the formula I, which process avoids the aforementioned disadvantages, and renders possible the safe production of benzofurazan-1-oxides of the formula I in a manner that is fully satisfactory from an ecological point of view.

It is suggested according to the present invention that the reaction of 2-nitroanilines of the formula II with alkali hypochlorite be performed in a two-phase reaction medium consisting of water and an organic solvent immiscible with water, in the presence of a phase-transfer catalyst.

Suitable organic solvents immiscible with water are aromatic hydrocarbons such as benzene, toluene or xylene, halogenated aromatic hydrocarbons such as chlorobenzene and dichlorobenzene, and also halogenated lower alkanes such as methylene chloride, chloroform, carbon tetrachloride and 1,2-dichloroethane. A preferred solvent is toluene.

Suitable phase-transfer catalysts are tetraalkylammonium salts, tetraalkylphosphonium salts, phenyltrialkylammonium salts, phenyltrialkylphosphonium salts, benzyltrialkylammonium salts and benzyltrialkylphosphonium salts. The following may be mentioned as examples of suitable phase-transfer catalysts: tetrabutylammonium bromide, tetrabutylammonium hydrogen sulfate, benzyltrimethylammonium chloride, benzyltriethylammonium bromide, hexadecyltrimethylammonium bromide, hexadecyltributylphosphonium bromide, tetrapropylammonium iodide, hexadecylpyridium chloride and dibenzo-18-crown-6. Particularly suitable phase-transfer catalysts are tetrabutylammonium halides and benzyltrimethylammonium halides, and also the corresponding hydrogen sulfates and tetrafluoroborates. The phase-transfer catalysts are used in amounts of 0.001 to 0.1 mole per mole of nitroaniline of the formula II, preferably 0.005 to 0.02 mole per mole of nitroaniline of the formula II.

Suitable 2-nitroanilines of the formula II are for example:

2-nitroaniline, 2-nitro-5-methylaniline, 2-nitro-4,5-dimethylaniline, 2-nitro-5-n-propylaniline,
2-nitro-5-ethylaniline,
2-nitro-5-n-butylaniline,
2-nitro-5-fluoroaniline,
2-nitro-5-chloroaniline, 2-nitro-5-bromoaniline,
2-nitro-4-chloro-5-methoxyaniline,
2-nitro-4-chloro-5-ethoxyaniline,
2-nitro-5-methoxyaniline,
2-nitro-5-ethoxyaniline,
2-nitro-5-n-propylaniline,
2-nitro-5isopropylaniline,
2-nitro-5-n-butylaniline,
2-nitro-5-methoxycarbonylaniline,
2-nitro-5-ethoxycarbonylaniline,
2-nitro-5-n-propoxycarbonylaniline,
2-nitro-5-n-butoxycarbonylaniline,
2-nitro-5-benzyloxycarbonylaniline,
2-nitro-5-carbamoylaniline,
2-nitro-(N',N'-dimethylcarbamoyl)-aniline,
2-nitro-5-(N',N'-diethylcarbamoyl)-aniline,
2-nitro-5-(N'-phenylcarbamoyl)-aniline,
2-nitro-5-[N'-(4'-phenyl)-carbamoyl]-aniline,
2nitro-5-[N'-(4'-methoxyphenyl)-carbamoyl]-aniline,
2-nitro-5-sulfamoylaniline,
2-nitro-5-(N',N'-dimethylsulfamoyl)-aniline,
2-nitro-5-(N',N'-diethylsulfamoyl)-aniline,
2-nitro-5-(N'-phenylsulfamoyl)-aniline,
2-nitro-5-[N'-(4-methylphenyl)-sulfamoyl]-aniline,
2-nitro-5-[N'-(4'-methoxyphenyl)-sulfamoyl]-aniline,
2-nitro-5-(N'-pyrid-2-yl-sulfamoyl)-aniline,
2-nitro-5-trifluoromethylaniline,
2-nitro-5-methylthioaniline,
2-nitro-5-ethylthioaniline,
2-nitro-5-n-propylthioaniline,
2-nitro-5-n-butylthioaniline,
2-nitro-5-methylsulfinylaniline,
2-nitro-5-ethylsulfinylaniline,
2-nitro-5-methylsulfonylaniline,
2-nitro-5-ethylsulfonylaniline,
2-nitro-5-phenoxyaniline,
2-nitro-5-(4'-methylphenoxy)-aniline,
2-nitro-5-(4'-methoxyphenoxy)-aniline,
2-nitro-5-phenylthioaniline,
2-nitro-5-(4'-methoxyphenylthio)-aniline,
2-nitro-5-phenylsulfinylaniline,
2-nitro-5-phenylsulfonylaniline,
2-nitro-4-chloro-5-methoxyaniline,
2-nitro-4-bromo-5-methoxyaniline,
2-nitro-4-chloro-5-phenoxyaniline,
2-nitro-4-chloro-5-(4'-methoxyphenoxy)-aniline,
2-nitro-4-chloro-5-phenylthioaniline,
2-nitro-4-methyl-5-phenylthioaniline,
2-nitro-4,5-dichloroaniline,
2-nitro-4,5-dibromoaniline,
2-nitro-5-benzyloxyaniline,
2-nitro-5-benzylthioaniline,
2-nitro-5-(2'-phenylethoxy)-aniline,
2-nitro-5-(2'-phenylethylthio)-aniline,
2-nitro-5-(2'-hydroxyethoxy)-aniline, and
2-nitro-5-(2'-dimethylaminoethoxy)-aniline.

The process according to the invention is performed at temperatures of −10 to +50° C., preferably at 10° to 20° C. Depending on the reaction temperature, the reaction time is 0.5 to 8 hours; in the preferred temperature range of 10° to 20° C. it is 1 to 3 hours.

Suitable alkali metal hypochlorites are in particular sodium hypochlorite and potassium hypochlorite. These alkali hypochlorites can be produced in a simple manner by introducing chlorine into sodium hydroxide solution or into potassium hydroxide solution.

After completion of the reaction, the formed benzofurazan-1-oxides of the formula I are in the organic phase. They can be isolated by separating the aqueous phase, and evaporating off the solvent. The isolation of the benzofurazan-1-oxides of the formula I which are present in the organic phase is however unnecessary since the solution obtained after separation of the aqueous phase can be used directly for further reaction to give quinoxaline-1,4-dioxides.

The method of procedure according to the invention avoids the disadvantages of the known process. The process according to the invention renders possible the safe production of benzofurazan-1-oxides of the formula I because it eliminates the dangers to safety associated with the formation of explosive esters of hypochlorous acid, and also the risks to safety attached to the isolation of the thermally unstable benzofurazan-1-oxides of the formula I. Furthermore, the further processing of the benzofurazan-1-oxides of the formula I produced according to the invention to quinoxaline-1,4-dioxides is simplified since the solution of the benzofurazan-1-oxide of the formula I, obtained after separation of the aqueous phase, can be used directly for this further reaction. The waste-water occurring during the process according to the invention contains moreover no organic solvent, which would have to be removed by costly operations.

The process according to the invention is further illustrated by the following Example.

EXAMPLE 1

Production of benzofurazan-1-oxide 18.4 kg (133 moles) of 2-nitroaniline and 0.42 kg (1.3 moles) of tetrabutylammonium bromide are dissolved in 70 kg of toluene. After the addition of 25.3 kg (226 moles) of 50% aqueous potassium hydroxide solution, there is added at 15° to 20° C., during one hour, 110 kg (185 moles) of an aqueous sodium hypochlorite solution. After the addition has been completed, the reaction mixture is allowed to react at 15° to 20° C. for 3 hours, and the aqueous phase is then separated. There is obtained in this manner a solution of benzofurazan-1-oxide in toluene, which solution is suitable for use directly for further reactions, for example for reaction with an acetoacetic acid derivative to the corresponding quinoxaline-1,4-dioxide.

Careful removal of the toluene by evaporation in vacuo yields 17.4 kg (96% of theory) of benzofurazan-1-oxide having a melting point of 68°–70° C.

I claim:

1. A process for producing benzofurazan-1-oxides of the formula I

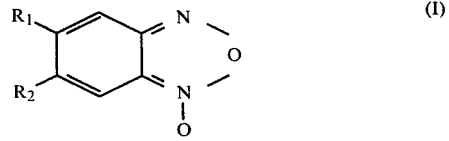

in which
R$_1$ and R$_2$ independently of one another each represent hydrogen, halogen, an alkyl group which has 1 to 4 carbon atoms and which can be substituted by halogen, hydroxyl, amino, alkylamino having 1 to 4 carbon atoms in the alkyl group and dialkylamino having 1 to 4 carbon atoms in each of the alkyl groups, or represents an alkoxy group having 1 to 4 carbon atoms, an alkylthio group having 1 to 4 carbon atoms, an alkoxycarbonyl group having 1 to 4 carbon atoms in the alkyl group, carbamoyl, N-alkylcarbamoyl having 1 to 4 carbon atoms in the alkyl group, N,N-dialkylcarbamoyl having 1 to 4 carbon atoms in each of the alkyl groups, sulfamoyl, N-alkylsulfamoyl having 1 to 4 carbon atoms in the alkyl group, N,N-dialkylsulfamoyl having 1 to 4 carbon atoms in each of the alkyl groups, a carboxyl group or a cyano group, and either the radical $R_1$ or the radical $R_2$ can additionally represent a group of the formula

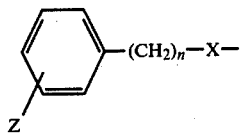

wherein Z represents hydrogen, halogen, an alkyl group having 1 to 4 carbon atoms, an alkoxy group having 1 to 4 carbon atoms, an alkylthio group having 1 to 4 carbon atoms or a trifluoromethyl group, n represents 0, 1 or 2, and X represents oxygen, sulfur, a sulfinyl group or a sulfonyl group, by reaction of 2-nitroanilines of the formula II

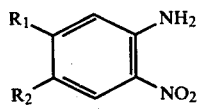

(II), in which $R_1$ and $R_2$ have the meanings given under the formula I, with alkali metal hypochlorite, in the presence of an alkali metal hydroxide, in which process the reaction of 2-nitroanilines of the formula II with alkali metal hypochlorite is performed in a two-phase reaction medium consisting of water and an organic solvent immiscible with water, in the presence of a phase-transfer catalyst.

2. A process according to claim 1, wherein the employed organic solvent immiscible with water is an aromatic hydrocarbon, a halogenated aromatic hydrocarbon or a halogenated lower alkane.

3. A process according to claim 1, wherein the employed organic solvent immiscible with water is benzene, toluene, xylene, chlorobenzene, dichlorobenzene, methylene chloride, chloroform, carbon tetrachloride or 1,2-dichloroethane.

4. A process according to claim 1, wherein the employed organic solvent immiscible with water is toluene.

5. A process according to claim 1, wherein the phase-transfer catalyst used is a tetraalkylammonium salt or a tetraalkylphosphonium salt.

6. A process according to claim 1, wherein the phase-transfer catalyst used is a tetrabutylammonium halide or a benzyltrimethylammonium halide or a corresponding hydrogen sulfate or tetrafluoroborate.

7. A process according to claim 1, wherein the phase-transfer catalyst is used in an amount of 0.001 to 0.1 mole per mole of nitroaniline of the formula II.

8. A process according to claim 1, wherein the phase-transfer catalyst is used in an amount of 0.005 to 0.02 mole per mole of nitroaniline of the formula II.

9. A process according to claim 1, wherein the reaction of a nitroaniline of the formula II with an alkali metal hypochlorite is performed at temperatures of $-10°$ to $+50°$ C.

10. A process according to claim 1, wherein the alkali metal hypochlorite used is sodium hypochlorite or potassium hypochlorite.

11. The process of claim 9, wherein said reaction temperature is from about 10° to 20° C.

* * * * *